(12) United States Patent
Liebig et al.

(10) Patent No.: US 11,382,778 B2
(45) Date of Patent: Jul. 12, 2022

(54) VASOSPASM TREATMENT

(71) Applicants: Femtos GmbH, Bochum (DE); Charité—Universitätsmedzin Berlin, Berlin (DE)

(72) Inventors: Thomas Liebig, Munich (DE); Hermann Monstadt, Bochum (DE); Hans Henkes, Stuttgart (DE); Ralf Hannes, Dortmund (DE)

(73) Assignees: Femtos GmbH, Bochum (DE); Charité—Universitätsmedizin Berlin, Berlin (DE)

( * ) Notice: Subject to any disclaimer, the term of this patent is extended or adjusted under 35 U.S.C. 154(b) by 0 days.

(21) Appl. No.: 16/306,500

(22) PCT Filed: Jun. 1, 2017

(86) PCT No.: PCT/EP2017/063302
§ 371 (c)(1),
(2) Date: Nov. 30, 2018

(87) PCT Pub. No.: WO2017/207689
PCT Pub. Date: Dec. 7, 2017

(65) Prior Publication Data
US 2019/0110912 A1  Apr. 18, 2019

(30) Foreign Application Priority Data
Jun. 2, 2016 (DE) .......................... 102016110199.0

(51) Int. Cl.
*A61F 2/91* (2013.01)
*A61F 2/90* (2013.01)
*A61F 2/95* (2013.01)

(52) U.S. Cl.
CPC .................. *A61F 2/91* (2013.01); *A61F 2/90* (2013.01); *A61F 2/95* (2013.01);
(Continued)

(58) Field of Classification Search
CPC .......................... A61F 2/95; A61B 2017/2215
See application file for complete search history.

(56) References Cited

U.S. PATENT DOCUMENTS

| 5,449,372 A | * | 9/1995 | Schmaltz | A61F 2/88 606/198 |
| 6,258,032 B1 | * | 7/2001 | Hammesfahr | A61B 8/06 600/454 |

(Continued)

FOREIGN PATENT DOCUMENTS

| CN | 103153214 | 6/2013 |
| CN | 104168844 | 11/2014 |

(Continued)

OTHER PUBLICATIONS

International Search Report from IA No. PCT/EP2017/063302 dated Aug. 31, 2017.
(Continued)

*Primary Examiner* — Katherine M Shi
*Assistant Examiner* — Lindsey Bachman
(74) *Attorney, Agent, or Firm* — Crockett & Crockett, PC; K. David Crockett, Esq.

(57) ABSTRACT

The invention relates to a device (1) having a stent structure (2) intended for the insertion into blood vessels of the human or animal body, wherein the stent structure (2) assumes an expanded state during which it is in contact with the inner wall of the blood vessel and a contracted state during which the stent structure being located in a microcatheter can be moved through the blood vessel, wherein the stent structure (2) preferably being connected at its proximal end with an delivery wire (3) and wherein the device (1) being employed for the treatment of vasospasm. Moreover, the invention also relates to a relevant method for the treatment of vasospasm.

6 Claims, 4 Drawing Sheets

(52) U.S. Cl.
CPC ............. *A61F 2210/0014* (2013.01); *A61F 2230/0006* (2013.01); *A61F 2230/0019* (2013.01); *A61F 2230/0091* (2013.01); *A61F 2250/0015* (2013.01); *A61F 2250/0036* (2013.01); *A61F 2250/0039* (2013.01); *A61F 2250/0067* (2013.01); *A61F 2250/0098* (2013.01)

(56) References Cited

U.S. PATENT DOCUMENTS

| | | | | |
|---|---|---|---|---|
| 8,529,596 | B2* | 9/2013 | Grandfield | A61B 17/320725 606/127 |
| 2014/0343585 | A1* | 11/2014 | Ferrera | A61B 17/221 606/159 |
| 2015/0313736 | A1 | 11/2015 | Berez et al. | |
| 2016/0081825 | A1 | 3/2016 | Sudin et al. | |
| 2017/0086992 | A1* | 3/2017 | Ferrera | A61M 25/09 |

FOREIGN PATENT DOCUMENTS

| | | | |
|---|---|---|---|
| DE | 10301850 | * | 7/2004 |
| EP | 1604697 | * | 12/2005 |
| EP | 2825129 | | 1/2015 |
| JP | 10005343 | | 1/1998 |
| JP | 2006521881 | | 9/2006 |
| JP | 2010264261 | | 11/2010 |
| JP | 2012510352 | | 5/2012 |
| JP | 2012532687 | | 12/2012 |
| JP | 2015504735 | | 2/2015 |
| WO | WO2011082319 | | 7/2011 |
| WO | WO2013138789 | | 9/2013 |

OTHER PUBLICATIONS

First Office Action dated Mar. 2, 2020 from Chinese Patent Application No. 201780034478.8.

Notice of Refusal dated Mar. 11, 2021 from Japanese Patent Application No. 2018-562307.

Office Action dated Aug. 17, 2021 from Japanese Patent Application No. 2018-562307.

Examination Report dated Jul. 30, 2021 from Indian Patent Application No. 201847045223.

* cited by examiner

VASOSPASM TREATMENT

The invention relates to a device having a stent structure intended for the insertion into blood vessels of the human or animal body, wherein the stent structure assumes an expanded state during which it is in contact with the inner wall of the blood vessel and a contracted state during which the stent structure being located in a microcatheter can be moved through the blood vessel, wherein the stent structure preferably being connected at its proximal end with an delivery wire.

Vascular endoprostheses, so-called stents, are often employed for the treatment of vasoconstrictions and are permanently implanted at the location of the constriction with a view to keeping the vessel lumen open. Typically, stents have a tubular structure and are either made by laser cutting to achieve a surface consisting of braces with openings between them or they consist of a wire braiding. Stents can be moved by means of a catheter to the placement site where they are expanded; in the event of self-expanding stents made of shape-memory material, expansion and contact with the inner wall of the vessel take place automatically. Alternatively, stents may also be caused to expand with the aid of balloons onto which the stent is crimp-mounted, or by other mechanical methods. After final placement, only the stent remains at the target site; catheter, guide or pusher wires, and other auxiliary means are removed from the blood vessel system.

Implants of basically similar design are also used for the occlusion of aneurysms in that they are placed in front of the neck of an aneurysm. However, such flow diverters have a higher surface density than stents for the elimination of stenoses. An example of a flow diverter has been described in publication WO 2008/107172 A1.

A spasmodic constriction of a blood vessel is known as vasospasm. Vasospasms involve the risk of blood no longer being supplied to downstream vessels (ischemia) which may lead to necrosis of the tissue thus cut off from perfusion. Especially in the cerebral region vasospasm may occur some days after a subarachnoid hemorrhage. In this respect, vasospasm is one of the main reasons for apoplexy in this region or even mortalities occurring after rupturing of an aneurysm and/or bleeding from it or as a result of an operation.

Usually, vasospasm is treated with medication, in particular calcium channel blockers or drugs are put to use that cause the NO level in the blood to increase. An example of a calcium channel blocker is nimodipine which is frequently used after subarachnoid hemorrhages with a view to preventing vasospasms. However, a medication-based treatment is associated with significant side effects and, moreover, is both cost-intensive and time-consuming.

It is thus the objective of the invention to provide means that allow vasospasm to be treated in some other way.

This objective is achieved by the invention proposing a device having a stent structure intended for the insertion into blood vessels of the human or animal body, wherein the stent structure assumes an expanded state during which it is in contact with the inner wall of the blood vessel and a contracted state during which the stent structure being located in a microcatheter can be moved through the blood vessel, wherein the stent structure preferably being connected at its proximal end with an delivery wire and the device being employed for the treatment of vasospasm.

Surprisingly, it has become evident that stent-like structures are conducive to the treatment of vasospasm. In contrast to the application possibilities of a stent for the treatment of stenoses or aneurysms as described hereinbefore, the stent structure is not intended to permanently remain within the blood vessel, i.e. it is not implanted but only placed in position temporarily and removed after a few minutes. Therefore, a detachment or severance point between the stent structure and the delivery wire is not required.

The stent structure is preferably of self-expanding design and capable of automatically assuming its expanded state after deployment from the microcatheter. To achieve this, a stent structure is of advantage that is made of a material having shape-memory properties, and in particular the use of nickel-titanium alloys known under the tradename of nitinol has proven its worth. However, also conceivable are polymers having shape-memory characteristics or other alloys.

The device proposed by the invention may, in particular, be used in the neurovascular field, it may, however, also be employed in the cardiovascular or peripheral region.

Typically, the delivery wire is a pusher wire, also known as guidewire. Such pusher wires are also used in a similar manner for the placement of implants that are intended to remain permanently in the vessel system in which case, however, the pusher wire is connected to the implant via a severance point, and said severance point may be designed for a mechanical, thermal, or electrolytic detachment. In accordance with the invention the device is only temporarily moved to the site where vasospasm has occurred and where expansion of the stent structure takes place. The delivery wire is preferably made of stainless steel, nitinol or a cobalt-chrome alloy.

The delivery wire or pusher wire is preferably attached radially outward to the proximal end of the stent structure. In other words, the connection between delivery wire and stent structure is not in the center of the stent structure but arranged eccentrically at or near the inner wall of the vessel. In this manner, the flow of blood is impeded to a minor degree only. What is more, an eccentric arrangement of the delivery wire facilitates retraction of the device into the microcatheter.

The delivery wire may also be attached to the stent structure at several locations, preferably to the proximal end of the stent structure. The arrangement of several connection points on the stent structure results in a slightly higher impediment of the flow of blood due to the additional braces or wires extending in this case within the center of the blood vessel. This, on the other hand, enables the proximal end of the stent structure that terminates towards the delivery wire and thus no longer is in complete contact with the inner wall of the vessel and therefore does not exert significant radial forces on the inner wall to be kept shorter. An delivery wire connected to the stent structure at several locations usually has a more central configuration.

Usually, treatment is carried out such that the inventive device arranged inside a microcatheter is moved towards the placement site, i.e. the location where vasospasm has occurred. Following this, the microcatheter is retracted in proximal direction causing the deployment of the stent structure which now expands and touches the inner wall of the vessel and in this manner counteracts vasospasm. The stent structure is left at the placement site for a short time, typically for 1 to 10 minutes. Subsequently, the microcatheter is again moved in distal direction to embrace the stent structure following which the microcatheter together with the device is retracted. The treatment may be repeated on several days in succession.

The terms "proximal" and "distal" are to be understood such that they refer as proximal to parts that point towards the attending physician when inserting the device, and as distal to parts that point away from the attending physician. Typically, the device is thus moved forward in distal direction with the aid of a microcatheter. The term "axial" refers to the longitudinal axis of the device extending from proximal to distal while the term "radial" denotes levels/planes extending vertically thereto.

A treatment undertaken with the device proposed by the invention may at the same time be accompanied by a medication-based treatment, for example using nimodipine. This may in particular be applied intra-arterially at the site where vasospasm has occurred.

Basically, the stent structure may consist of individual, interconnected strings or braces. Such a stent structure can be manufactured by laser cutting technique in a manner known per se. In addition, it is thought expedient to process the stent structure by electropolishing to make it smoother and rounder and thus render it less traumatic. This also reduces the risk that germs or other impurities may adhere to the structure.

Alternatively, the stent structure may also be a mesh-like structure consisting of individual wires in the form of a braiding. The wires in this case typically extend helically along the longitudinal axis, with intersecting opposed wires extending above and below each other at points of intersection resulting in honeycomb-like openings being created between the wires. Preferably, the total number of wires ranges between 8 and 64. As wires forming the mesh structure individual wires made of metal may be employed but it is also possible to provide strands, i.e. several wires of small diameter arranged so as to form a filament, preferably twisted around each other.

An advantage of a stent structure comprising interconnected strings or braces that in particular are produced by laser cutting techniques over a mesh structure consisting of wires is that during the expansion process a stent structure of braces will be less prone to longitudinal contraction than a mesh structure. Longitudinal contraction should be kept to a minimum because the stent structure exerts additional stress on the surrounding vessel wall during longitudinal contraction. Due to the fact that vasospasm is especially caused by stimuli acting on the vessel any additional stress has to be avoided in the treatment of vasospasm.

A stent structure of interconnected braces moreover offers advantages in that the radial force exerted by such a stent structure of otherwise comparable construction, braces/wire density and braces/wire thickness is higher than that of a mesh structure consisting of wires. The reason for this that the braces at the points of intersection are permanently attached to each other, whereas the wires in a mesh structure as a rule only extend above and below each other.

The braces or wires may have a round, oval, square or rectangular cross section, with the edges being advantageously rounded off in the event of a square or rectangular cross section.

The openings thus formed within the stent structure between the individual braces or wires should have an inscribed circle diameter ranging between 0.1 and 6 mm, where under inscribed circle diameter the diameter of the largest possible circle is to be understood that can be placed in the opening. The above data apply to a stent structure which is in expanded state, i.e. in the state the stent structure assumes when it is not exposed to external constraints.

Preferred are openings having an inscribed circle diameter of 1 mm, which translates into a relatively coarse-meshed stent structure, because such a structure is capable of exerting a radial force of a magnitude suitable for the treatment of vasospasm. For example, the openings/cells of a stent structure having a diameter of between 3 and 5 mm in expanded state may have an inscribed circle diameter ranging between 2 and 4.5 mm.

The openings provided in the stent structure should be closed all around, that is should without interruptions be fully surrounded or embraced by braces or wires (the so-called closed-cell design) because when treatment has been completed this will facilitate bringing the stent structure into the microcatheter by moving the catheter forward.

Moreover, in the interest of producing a radial force of suitable magnitude it is considered expedient to use braces or wires having a relatively large cross section or diameter, i.e. using relatively massive braces/wires. When braces or wires of an essentially rectangular cross section were put to use, it has turned out to be of advantage to provide braces/wires of a height and width of between 30 and 300 µm, with a rectangular cross section the edges of which were rounded also being considered as essentially rectangular. In the event of a round cross section the diameter should range between 30 and 300 µm. Normally, the stent structure is of open design at the proximal end. At its distal end, the stent structure may also be open but can also be of closed design. A stent structure that is open at both ends offers the advantage that the blood flow is impeded as little as possible so that an undersupply of downstream blood vessels and tissue they supply with blood can be prevented. On the other hand, providing the distal end with a closed structure is more atraumatic. It is to be noted that referring to an open structure means there are no braces or wires at the respective end of the stent structure and that braces/wires are only arranged over the outer circumference of the stent structure. In case of a closed end, however, braces or wires also exist in the center of the stent structure. However, since there are still openings between the braces or wires, even a closed distal end is not completely impervious and still allows the flow of blood through the respective openings.

An antithrombogeneous coating applied to the inside of the stent structure is considered expedient because the structure stays within the blood vessel for a certain time span during which the prevention of clots is mandatory that might form in the vessel already constricted due to vasospasm that has occurred. The outside of the stent structure could advantageously be coated with an agent conducive to vessel relaxation, for example with a calcium channel blocker such as nimodipine.

Even if an antithrombogeneous coating in particular applied to the inside of the stent structure and a vessel relaxing coating in particular applied to the outside of the stent structure are beneficial and helpful, such an antithrombogeneous or vessel relaxing coating can also be applied to the entire stent structure or the braces/wires can be provided with a respective coating on all sides. In this case, the respective coating is not applied exclusively to the inside or outside of the stent structure.

Generally speaking, it is to be noted that all relevant coatings may also cover only a certain part or a partial length of the stent structure. Coatings are of significance especially in those areas of the stent structure that are in contact with the inner wall of the vessel, i.e. essentially the cylindrical part of the stent structure.

The force that the expanding stent structure exerts radially outward on the inner vessel wall should range between 2 and 16 N/m, preferably between 5 and 8 N/m. The radial force specified in this case denotes the force radially exerted per unit of length, i.e. is to be viewed as relative radial force. In this case, only that part of the stent structure is to be taken into account that is in contact with the inner wall of the vessel and is thus capable of exerting forces on it (effective length). Along the effective length, the stent structure must cover a minimum of 50% of an envelope arranged around the stent structure. Contrary to this, the absolute radial force denotes the value applicable to the entire stent structure.

The exerted radial force (chronic outward force, COF) is determined by means of a V-block test as described below:

The V-block testing apparatus consists of two polymethyl methacrylate (PMMA) blocks in which a 90° vee-groove each has been milled and then smoothly polished. These V-blocks are placed one on top of the other in such a way that when in contact a hollow space of square cross section is created between the blocks. Whereas one of the V-blocks is firmly secured the other is provided with a force sensor. COF denotes the force the stent structure upon self-expansion exerts on the blood vessel or during testing on the V-blocks. For radial force determination, the stent structure located inside a transportation hose or microcatheter is placed centrally between the V-blocks. Following this, the transportation hose/microcatheter is retracted causing the stent structure to be released. Due to its self-expanding properties, the structure folds out and the radial force it then produces can be measured by means of the force sensor connected to one of the V-blocks and further evaluated. To enable stent structures of different lengths to be compared the relative radial force is calculated as follows:

$$COFrel. = \frac{COFabs.}{\text{effective length of the stent structure}}$$

As per an advantageous embodiment the radial force exerted over the length by the stent structure in expanded state is essentially constant, i.e. in the proximal as well as distal section it coincides with the radial force of the middle section. Compared to customary, uniformly designed stents, however, the radial force actually effective in the proximal and distal sections in most cases is weaker than in the middle section. For that reason, it is expedient to purposefully increase the radial force acting in the proximal and distal sections with a view to creating a stent structure the radial force of which being essentially constant over the effective length in expanded state, with the proximal end of the stent structure where, typically, the braces or wires are no longer in complete contact with the inner wall of the vessel being left unconsidered as far as radial force is concerned. Therefore, the proximal end is thus seen as part of the stent structure located farthest in proximal direction that no longer forms part of the effective length and where the braces/wires extend towards the delivery wire. A typical length of this proximal end amounts to 8 to 10 mm, that means the overall length of the stent structure is roughly longer by this amount than the effective length of the stent structure.

To increase the radial force in the proximal and distal sections, the braces or wires may be designed to have a larger cross section here than in the middle section. The braces/wires are thus made more massive which fully or to some degree compensates the inherent tendency of a stent structure to exert higher radial forces in the middle section.

Alternatively or in addition, the density of the braces or wires can be arranged so as to be higher in the proximal section than in the middle section. This step also ensures that the reduction of the radial force as observed in customary stents to diminish towards proximal or distal can fully or to some extent be compensated.

Another possibility is to provide a slot in the stent structure extending helically over the generated surface of the stent structure or in longitudinal direction along the generated surface of the stent structure. In this way, individual braces or wires may extend over the slot with a view to influencing the radial force characteristics.

Typically, the diameter of the stent structure in expanded state is in the range of between 2 and 8 mm, preferably ranges between 4 and 6 mm. The total length of the stent structure in expanded state as a rule amounts to 5 to 50 mm, preferably lies between 10 and 45 mm, further preferred between 20 and 40 mm. The effective length, i.e. the length of the stent structure in expanded state that actually exerts radial forces on the inner wall of the vessel, is in most cases shorter by approx. 8 to 10 mm.

Meaningfully, the device is provided with one or several radiopaque markers allowing the attending physician to visualize the treatment. The radiopaque markers may, for example, consist of platinum, palladium, platinum-iridium, tantalum, gold, tungsten or other metals opaque to radiation. Radiopaque coils may, for instance, be arranged in the device at various points. As another alternative, the stent structure, and in particular the braces or wires of the stent structure, may be provided with a coating consisting of radiopaque material, for example with a gold coating which may, for instance, have a thickness of between 1 and 6 µm. The coating consisting of a radiopaque material need not be applied to the entire stent structure; it is of significance, however, especially in areas of the stent structure in contact with the inner wall of the vessel, that is primarily in the cylindrical part of the stent structure. Nevertheless, even when applying a radiopaque coating it is considered expedient to arrange one or several radiopaque markers in the device, in particular at the distal end of the stent structure.

Aside from the inventive device the invention also relates to a method for the treatment of vasospasm, for which purpose a device is used of the kind described hereinbefore. Said method provides for the stent structure to be navigated to the vasospasm site by means of the delivery wire and expanded there, which as a rule is achieved by retracting the microcatheter accommodating the device, said retraction taking place in proximal direction. At the site where vasospasm has occurred the stent structure remains for some minutes, preferably for a period of between 1 and 10 minutes. Afterwards, the stent structure is removed from the blood vessel. For this purpose, the microcatheter can be pushed forward in distal direction to again embrace the stent structure and accommodate it within the microcatheter. Microcatheter and device are then ready to be retracted and removed from the blood vessel system. It is advisable to repeat the described approach several days in succession to continue the vasospasm treatment.

Any and all statements made with respect to the device shall equally apply in the same way as well to the method and vice versa.

Further elucidation of the invention is provided through the enclosed figures where FIG. 1*a* is a side view of a device proposed by the invention;

FIG. 1*b* shows the inventive device of FIG. 1*a* as a developed representation;

Figure 1A:
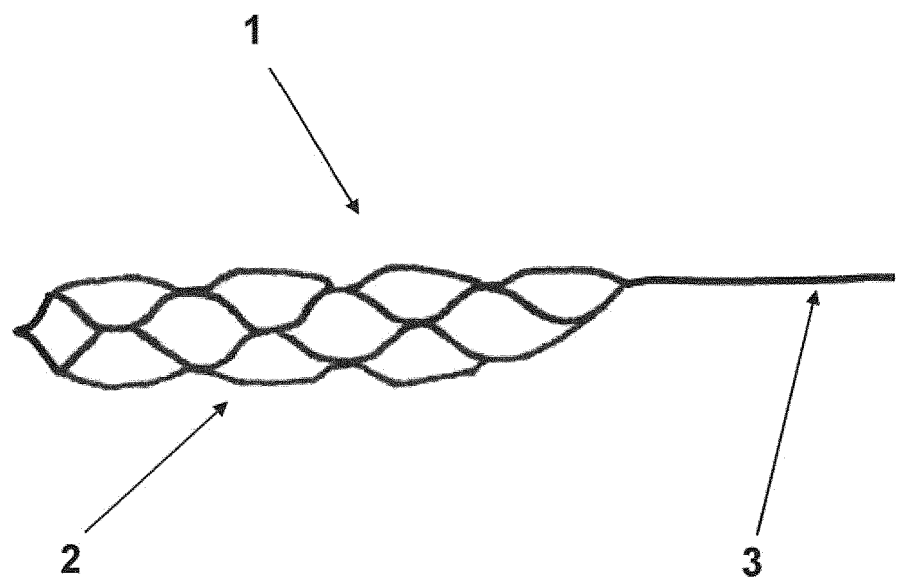

In FIG. 1a the inventive device 1 is illustrated in the form of a side view. The device has a stent structure 2 and an delivery wire 3 in the form of a pusher wire. In this example, the stent structure 2 is made by laser cutting and comprises braces that in their entirety form a continuous honeycomb structure. The delivery wire 3 is eccentrically attached, i.e. peripherally connected to the proximal end of stent structure 2.

Figure 1B:
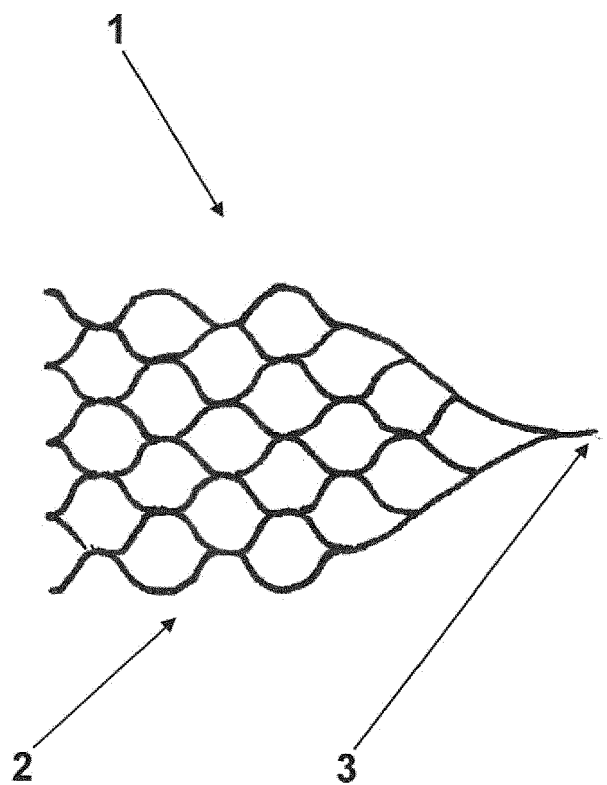

In FIG. 1b the device 1 of FIG. 1a is shown as a developed representation, i.e. depicting the hypothetical situation that would arise if the essentially cylindrical stent structure 2 as shown in FIG. 1a was cut open along the longitudinal axis and spread so as to be planar. In this case, only a short portion of delivery wire 3 has been shown.

Figure 2:
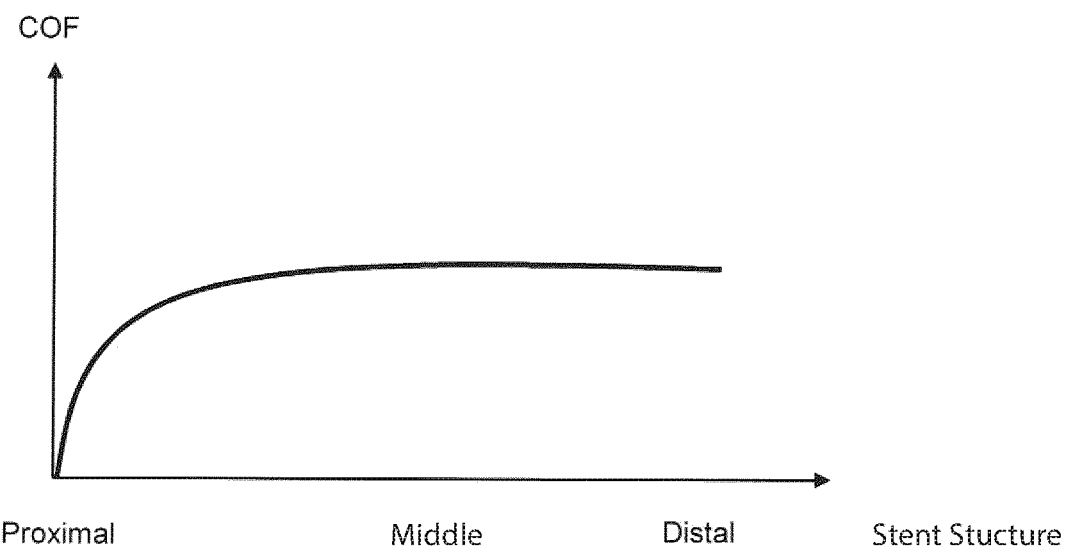
FIG. 2 is a representation of the radial force level along the stent structure.
Figure 3:
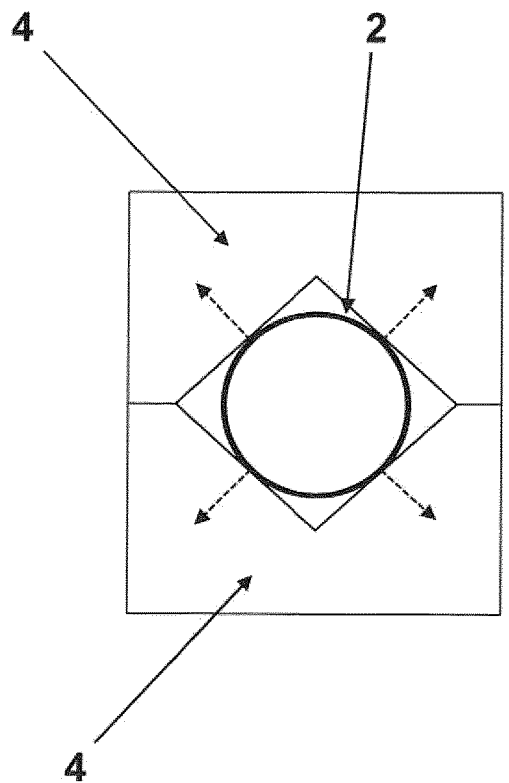
FIG. 3 shows a measuring apparatus for the determination of radial forces exerted by the stent structure.

In FIG. 2 the characteristic of the radial force (COF) along the stent structure 2 is shown on the basis of a preferred embodiment. Only at the proximal end acts a lower radial force on the surrounding inner wall of the vessel, otherwise the radial force is constant over the entire stent structure 2. The radial force reduction encountered at the proximal end is due to the fact that the stent structure 2 at this location terminates at a single point in delivery wire 3 resulting in the stent structure 2 being unable to fully cover the inner vessel wall circumferentially.

n apparatus for the determination of the radial force by means of a V-block test is shown in FIG. 3 for the stent structure 2. The apparatus for radial force determination comprises two V-blocks 4, each of which provided with a 90° vee-groove. Positioning one of the V-blocks 4 on the other results in a hollow space of square cross section to be created. While the lower V-block 4 is firmly secured, the top V-block 4 is provided with a force sensor for radial force determination.

For testing purposes, stent structure 2 accommodated in a transportation hose or microcatheter is at first placed into the square hollow space between the V-blocks 4. Following this, the hose/microcatheter is retracted such that the self-expanding stent structure 2 is allowed to expand thus contacting the surfaces of the V-block 4. The forces exerted by the stent structure 2 are signified by the broken arrow lines and are transmitted to the force sensor via the V-blocks 4 and finally evaluated.

Figure 4:
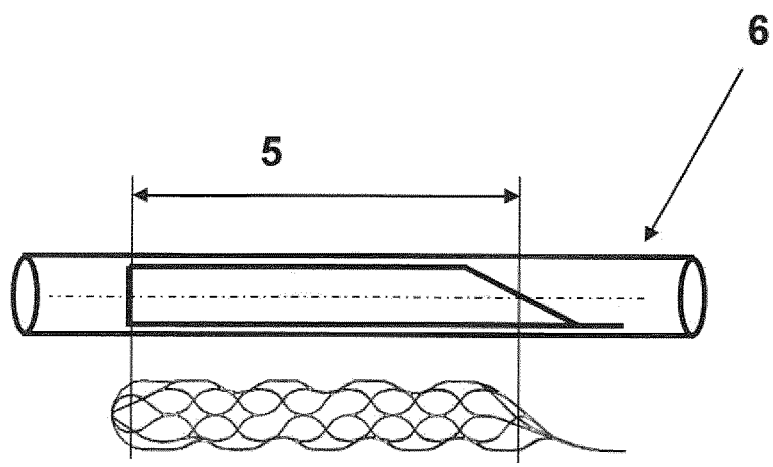
FIG. 4 illustrates the determination of the effective length of the stent structure.

As already mentioned, the relative radial force variable is used to enable stent structures 2 of different length to be compared, i.e. the absolute radial force relevant to the effective length 5 of the stent structure 2. As illustrated in FIG. 4, for the determination of said effective length 5, the stent structure is drawn into a transparent tube 6 having a circular cross section. The effective length 5 is the length where the stent structure 2 at least covers 50% of the circumference. It is to be noted that in particular the proximal end of stent structure 2 where the structure terminates towards the delivery wire does no longer form part of the effective length 5.

Figure 5:
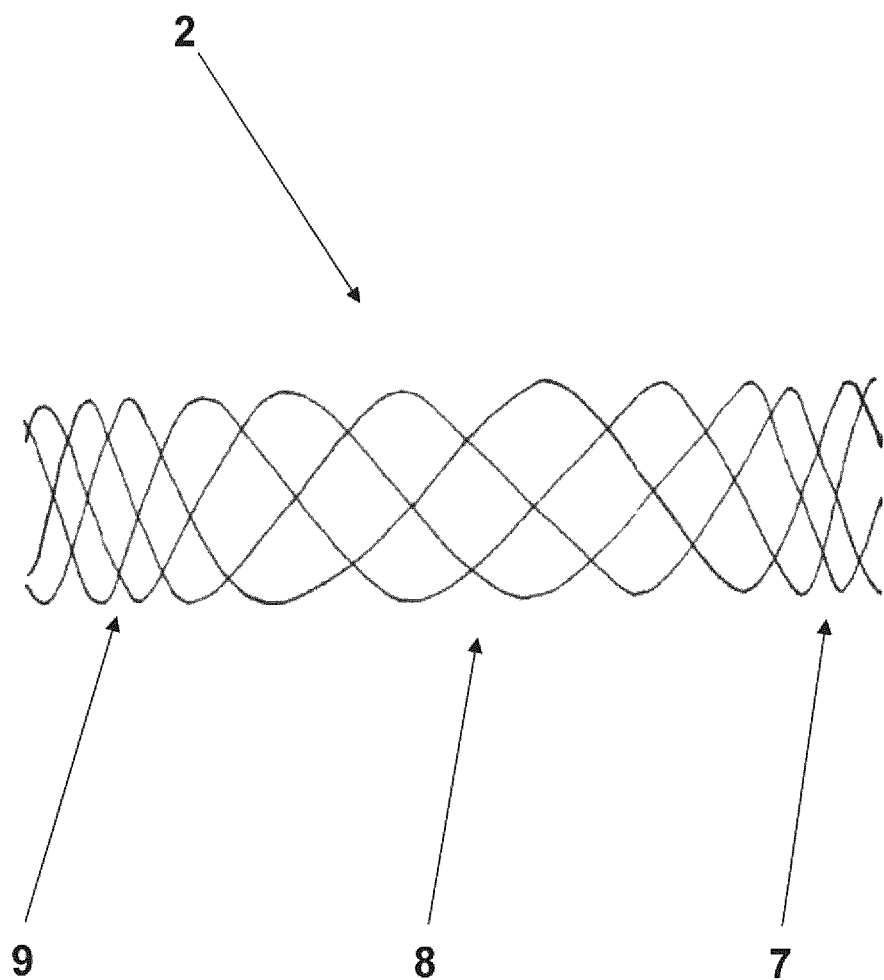
FIG. 5 is a side view of a preferred embodiment of the stent structure.

In FIG. 5 a preferred embodiment of an inventive stent structure 2 is finally illustrated as a side view, wherein the stent structure 2 is composed of a proximal section 7, a middle section 8, and a distal section 9. The view is limited to show the effective length 5, that is neither the proximal end nor the delivery wire is shown. Other than shown in FIG. 1 this is a stent structure 2 consisting of individual wires forming a mesh structure. To achieve a uniform characteristic of the radial force over the entire effective length 5 as depicted in FIG. 2, the density of the mesh structure has been increased both in the proximal section 7 and in distal section 9 as compared with the middle section 8. This results in the radial force reduction in the proximal and distal region frequently observed with uniformly built up stent structures 2 to be compensated by providing a wire arrangement of higher density.

The invention claimed is:

1. A method for the treatment of vasospasm, said method comprising the steps of:
providing a stent structure having a proximal section, a middle section, and a distal section, and a proximal end, said proximal end being secured to a delivery wire; wherein
the proximal section, a middle section, and a distal section of the stent structure comprise an effective length of the stent structure that, in an expanded state, is in contact with the inner wall of the vessel and covers a minimum of 50% of an envelope arranged around the stent structure; and wherein
the entire effective length of the stent structure, in the expanded state, exerts an essentially constant radial force on an inner wall of the vessel; and
navigating the stent structure to a vasospasm site within a blood vessel of a patient using the delivery wire, and expanding the stent structure at the vasospasm site; and
maintaining the stent structure at the vasospasm site for 1 to 10 minutes, and thereafter removing the stent structure from the blood vessel.

2. The method according to claim 1, wherein the treatment of vasospasm by means of the stent structure is repeated on several days in succession.

3. The method of claim 1, wherein the force exerted radially outward by the expanded stent structure amounts to between 2 and 16 N/m.

4. The method of claim 1, wherein the force exerted radially outward by the expanded stent structure amounts to between 5 and 8 N/m.

5. The method of claim 1, wherein the stent structure comprises wires forming a mesh structure, and wires in the proximal and distal sections have a larger cross section than wires in the middle section.

6. The method of claim 1, wherein the stent structure comprises wires forming a mesh structure, and the density of wires in the proximal and distal sections is higher than the braces or wires in the middle section.

* * * * *